(12) United States Patent
Frankin et al.

(10) Patent No.: US 8,043,506 B2
(45) Date of Patent: Oct. 25, 2011

(54) PROCESS AND REACTOR FOR ANAEROBIC WASTE WATER PURIFICATION

(75) Inventors: Robertus Johannes Frankin, Cilandak Jakarta (ID); Michaël Johannes Otten, Pondok Indah Jakarta (ID)

(73) Assignee: Biothane Systems International B.V., Delft (NL)

( * ) Notice: Subject to any disclaimer, the term of this patent is extended or adjusted under 35 U.S.C. 154(b) by 400 days.

(21) Appl. No.: 12/159,986

(22) PCT Filed: Jan. 5, 2007

(86) PCT No.: PCT/NL2007/000003
§ 371 (c)(1),
(2), (4) Date: Mar. 2, 2009

(87) PCT Pub. No.: WO2007/078195
PCT Pub. Date: Jul. 12, 2007

(65) Prior Publication Data
US 2009/0223890 A1    Sep. 10, 2009

(30) Foreign Application Priority Data
Jan. 5, 2006   (EP) .................................... 06075014

(51) Int. Cl.
*C02F 3/28* (2006.01)
(52) U.S. Cl. ..... 210/603; 210/617; 210/259; 210/532.1; 210/539
(58) Field of Classification Search ................. 210/603, 210/615, 616, 617, 622, 252, 259, 521, 532.1, 210/539
See application file for complete search history.

(56) References Cited

U.S. PATENT DOCUMENTS

| | | | | |
|---|---|---|---|---|
| 5,616,241 A | * | 4/1997 | Khudenko | .................... 210/151 |
| 5,733,454 A | * | 3/1998 | Cummings | .................... 210/603 |
| 2003/0150786 A1 | | 8/2003 | Verink | |

FOREIGN PATENT DOCUMENTS

| | | |
|---|---|---|
| DE | 10 2004 021 022 | 10/2005 |
| EP | 0 311 216 | 4/1989 |
| EP | 0 808 805 | 11/1997 |
| EP | 1 408 008 | 4/2004 |

(Continued)

OTHER PUBLICATIONS

International Search Report for PCT/NL2007/000003, mailed on May 2, 2007, 2 pages.

(Continued)

*Primary Examiner* — Fred Prince
(74) *Attorney, Agent, or Firm* — Morrison & Foerster LLP (57) ABSTRACT

The invention is directed to a process for the anaerobic purification of waste water using a sludge bed system, which process comprises feeding waste water, and optionally recycle water, to the lower part of an upflow reactor, containing mainly granular biomass thus producing biogas in the treatment passing the resulting gas/liquid/solid mixture upward and separating the gas and solid from the liquid in a three phase separator and thereby generating an anaerobic effluent that is withdrawn from the top of the separator, the improvement comprising separating the solids from the liquid in a separator, wherein, above the separation of the gas from the liquid phase, tilted plates, tubes or other tilted internals are installed in the three phase separator body to increase the effective settling surface, to an upflow reactor suitable for this process as well as to a three phase separator.

22 Claims, 7 Drawing Sheets

FOREIGN PATENT DOCUMENTS

| | | |
|---|---|---|
| JP | 60-235696 | 11/1985 |
| JP | 61-111200 | 5/1986 |
| JP | 01-218695 | 8/1989 |
| JP | 02-253898 | 10/1990 |
| JP | 04-341395 | 11/1992 |
| JP | 04-341396 | 11/1992 |
| JP | 05-123691 | 5/1993 |
| JP | 07-308686 | 11/1995 |
| JP | 09-220592 | 8/1997 |
| JP | 09-248593 | 9/1997 |
| JP | 10-511893 | 11/1998 |
| JP | 11-207384 | 8/1999 |
| JP | 2003-326294 | 11/2003 |
| JP | 2007-144401 | 6/2007 |
| WO | WO-96/32177 | 10/1996 |
| WO | WO-2005/095288 | 10/2005 |

OTHER PUBLICATIONS

International Preliminary Report on Patentability for PCT/NL2007/000003, issued on Jul. 8, 2008, 5 pages.

Written Opinion of the International Searching Authority for PCT/NL2007/000003, issued on Jul. 8, 2008, 4 pages.

* cited by examiner

FIGURE 1. GENERAL PROCESS ARRANGEMENT

FIGURE 2a. THREE PHASE SEPARATOR

SIDE VIEW

FIGURE 2b. THREE PHASE SEPARATOR (TOP VIEW)
WITH DIRECT RECYCLE PIPE

FIGURE 2c. THREE PHASE SEPARATOR (TOP VIEW)
DEDICATED SECTION FOR DIRECT RECYCLE

FIGURE 3. UPFLOW REACTOR WITH
MULTI LEVEL INFLUENT DISTRIBUTION SYSTEM

FIGURE 4a. DETAIL DIRECT RECYCLE PIPE (HOLES)

FIGURE 4b. DETAIL DIRECT RECYCLE PIPE (SLOTS)

FIGURE 5. MULTIPLE THREE PHASE SEPARATORS WITH NO / MAX FLOW SYSTEM

FIGURE 6. GAS DEFLECTING DEVICE

PROCESS AND REACTOR FOR ANAEROBIC WASTE WATER PURIFICATION

CROSS-REFERENCE TO RELATED APPLICATIONS

This application is the national phase of PCT application PCT/NL2007/000003 having an international filing date of 5 Jan. 2007, which claims benefit of European patent application no. 06075014.8 filed 5 Jan. 2006. The contents of the above patent applications are incorporated by reference herein in their entirety.

The present invention is in the area of biological waste water purification and more in particular in the use of sludge bed systems in anaerobic waste water purification.

Biological wastewater treatment uses active biomass (bacteria) to convert the pollutants (organic substances) to harmless components.

Basically there are two types of bacteria that can perform this treatment. For so-called anaerobic treatment (without oxygen) a consortia of anaerobic bacteria convert pollutants substantially to biogas.

In aerobic treatment the pollutants are reduced under aerobic (with oxygen) conditions for a great extend to new bacteria/biomass (surplus sludge) which needs then to be separated from the treated wastewater and processed separately.

Anaerobic sludge bed reactor systems utilise anaerobic bacteria to convert pollutants in wastewater to biogas. These anaerobic bacteria mainly grow in aggregates, often referred to as granular biomass. The systems are often characterised by low net biomass production (typically 2-4% of converted COD) as a result of the low net yield of anaerobic bacteria involved.

This is on one hand a big advantage, as the excess biomass developed in wastewater treatment systems has to be disposed as a solid waste, at significant cost, but it makes on the other hand a sensitive aspect to retain/maintain sufficient active biological sludge in the treatment system (reactor).

The method of retaining biomass in anaerobic treatment reactors can be done in various ways. The immobilization of biomass on a fixed or mobile carrier is one method to uncouple liquid retention time from biomass retention time.

A better and preferred method however is to make use of mainly granulated biomass as applied in UASB, EGSB and IC reactors.

To date more than 85% of any new industrial applications for high rate anaerobic treatment are based on anaerobic sludge bed technologies (Frankin R. J. (2001). *Full scale experiences with anaerobic treatment of industrial wastewater. Wat Sci. Tech.*, 44(8), 1-6).

The purification process generally comprises the use of a system wherein raw wastewater is introduced at the bottom of an upflow reactor, containing dispersed biomass in (partly purified) wastewater. During the anaerobic purification process biogas is produced and a mixture of liquid (water), solids (biomass) and gas flows upward in the reactor. Before purified wastewater can be discharged, a gas-liquid-solid separation has to take place.

A typical system for such a process is based on a conditioning tank to which the raw waste water is fed. A recycle of anaerobic effluent from the reactor is also fed (normally by gravity) to the conditioning tank. From the conditioning tank the mixture is introduced into the base of an upflow reactor through a special design influent distribution system. Subsequently the water flows upwards through the dense anaerobic sludge bed. Soluble COD is readily converted to biogas which is rich in methane and an upward circulation of water and gas borne sludge is established. The specially constructed three phase separator sections at the top of the reactor first of all allow effective degasification to occur. Next the solids particles, now devoid of attached gas bubbles, sink back to the bottom of the three phase separator and are returned to the reactor.

In sludge bed reactors the biomass is retained by virtue of the good settleability of such biomass and the use of a three phase separator or three phase separators in the reactor that can effectively separate (from the treated wastewater and the produced biogas) and retain such biomass in the reactor.

The object of the present invention is to provide an improved anaerobic wastewater treatment process based on sludge bed technology.

This is achieved by using a process and a reactor for anaerobic wastewater treatment with one or more of the following features of the improved system, which features comprise:

Improved sludge retention and performance by using an
  Improved anaerobic effluent recycle method
  improved three phase separator or three phase separators with:
    Tilted plates, tubes or other internals installed in the three phase separator body to increase the effective settling surface.
    In process cleaning facilities for the three phase separator or three phase separators and the internals.
    Multi plate gas separation baffles under the three phase separator or three phase separators to make the gas separation more effective.
  Improved influent distribution system(s).

In a first aspect the present invention resides in an improved separation of the solids for the liquid. In this embodiment a three phase separator is used, having tilted plates, tubes or other tilted internals installed in the three phase separator body with the aim to increase the effective settling surface without changing the volume.

Accordingly the invention is defined as a process for the anaerobic purification of waste water using a sludge bed system, which process comprises feeding waste water, and optionally recycle water, to the lower part of an upflow reactor, containing mainly granular biomass thus producing biogas in the treatment passing the resulting gas-liquid-solid mixture upward and separating the gas and solid from the liquid in a three phase separator and thereby generating an anaerobic effluent that is withdrawn from the top of the separator, the improvement comprising separating the solids form the liquid in a separator, wherein, above the separation of the gas from the liquid phase, tilted plates, tubes or other tilted internals are installed in the three phase separator body to increase the effective settling surface.

In a further embodiment thereof the invention is directed to an upflow reactor suitable for this process, which reactor comprises a reactor tank having incorporated therein three phase separators for separating gas, solid and liquid, which three phase separators are present in the upper part of the said reactor, influent distribution means for introducing a flow of waste water into the reactor, said influent distribution means being present in the lower part of the reactor, effluent withdrawal means for withdrawing anaerobic effluent from the separator and optionally recycle withdrawal means for withdrawing a recycle flow from the reactor, wherein the three phase separator has tilted plates, pipes or other tilted internals installed in the three phase separator body, above the separation of the gas from the liquid phase.

A third way of defining this invention is through a three phase separator, which separator comprises a main separator body, at least one entry for a gas-liquid-solid mixture, single or multiple-biogas separation baffle plates for separating gas from the mixture, tilted plates, pipes or other tilted internals installed in the three phase separator body, above the separation of the gas from the liquid phase, and means for withdrawing effluent and optionally also recycle water from the top of the three phase separator.

The internals in the separator are positioned in an angle of typically 50 to 70° to allow gravity settling of the collected solids and the free space between the plates, in the tubes or between the internals is typically at least 50 mm to prevent blockage. An important aspect herein is that the gas separation is located below these internals.

This can be further explained with the following example:
Design raw wastewater flow 100 m$^3$/h.
Actual wastewater flow 60 m$^3$/h
Feed flow to the reactor 150 m$^3$/h, so 50 m3/h anaerobic effluent recycle under design conditions
The reactor has 3 three phase separators of equal lengths each of 5 m$^2$ effective settling surface, without extra internals and 25 m$^2$ effective settling surface as a result of a package of tilted pipes ~100 no of pipes of Ø150 mm each, the pipes are positioned under an angle of 60°) in the three phase separator body).

The effective surface load on the three phase separator both for the design and actual situation is 100/15=6.67 m$^3$/m$^2$·hour in a conventional system. According to the invention the effective surface load on the three phase separator is 100/75=1.13 m$^3$/m$^2$·hour under design conditions and only 60/75=0.8 m$^3$/m$^2$·hour under actual operating conditions.

This is a big advantage both for a more effective process (better sludge inventory, better performance and reduction rates) and to achieve lower overall investment cost.

To realize the same surface load less three phase separator (surface) is required.

Recirculation of part of the anaerobic effluent is beneficial for stable operation of an anaerobic sludge bed process, reactor or device. It provides stable hydraulic conditions, recycle of alkalinity and nutrients and dilution of the raw feed/wastewater (to prevent toxicity and/or local overloading). In the current anaerobic sludge bed processes, reactors or devices it is common practice to recycle (part of) the anaerobic effluent by gravity back to a conditioning tank, after it has passed the complete three phase separator or three phase separators. This results in an extra surface load (expressed as m$^3$ water/m$^2$ three phase separator surface. hour) on the three phase separator or three phase separators, as the surface load is determined by the total feed to the reactor (=actual raw wastewater flow+recirculation flow) divided by the available net surface area of the three phase separator.

With the tilted internals of this invention already an important improvement is achieved. However, by combining this with an improved recycle method, even further improvement may be obtained.

Accordingly a preferred embodiment is withdrawing the recycle water separately from the effluent, either from the top of the reactor outside the three phase separator or from the three phase separator.

The novel aspect thereof is that the anaerobic effluent recycle is not taken from the three phase separator effluent, as is conventional, but from the top of the reactor outside the three phase separator, from a dedicated section of the three phase separator or preferably from the bottom of the three phase separator where the biogas has already been separated and the settled solids (from the three phase separator body) are collected.

There are various ways in which the recycle water can be withdrawn from the top of the reactor or the three phase separator. In a first embodiment, the recycle water is withdrawn from the separator at a location where the gas has already been separated off. This is preferably done from the bottom of the separator, just above gas deflecting plates.

In another embodiment, the recycle is withdrawn from the top of the reactor, outside the separator, i.e. from the solid-gas-liquid phase. In this embodiment it is also possible to locate the withdrawal behind a gas-deflecting device, such as a tilted plate, thereby providing some separation of the gas from the solid-gas-liquid mixture.

In yet another embodiment it is also possible to dedicate one or more of the three phase separators (provided more than one is present) or part of the three phase separators for the recycle whereas the remainder of the separators or parts of the three phase separators are solely dedicated as effluent producing separators.

The amount of recycle water (by volume) will generally be between >0 and 95% of the combined amount of recycle water and anaerobic effluent. Conversely, the amount of anaerobic effluent will be between 5 and <100% thereof.

As a result the effective surface load (m$^3$/m$^2$·hour) on the three phase separator is always the lowest possible and directly proportional to the actual raw wastewater feed flow.

Important advantages of the invention are the possibility to either design smaller three phase separators, which would reduce the investment cost, or to have a better performance of the three phase separator because of the lower hydraulic load thereof.

Quite often a number of three phase separators are present in a reactor. In such a situation it is important to have an effective and equal recycle of anaerobic effluent from each three phase separator and over the length/surface of each three phase separator.

In a further embodiment of the invention this is achieved by accomplishing the effluent recycle by a modulating min/max flow system.

Automatic open/close valves are then installed in the recycle lines/pipes from each three phase separator. In this way a full or partly recycle can be accomplished from each three phase separator or pipe separately. In other words, in this embodiment the recycle flow from each three phase separator is controlled by the valves with which the distribution of the amount of recycle from each three phase separator is determined.

In the first embodiment each three phase separator contains an anaerobic effluent recirculation collection pipe at the bottom, with several openings/slots (in the three phase separator) over its lengths.)

Each pipe is extended through the walls of respectively the three phase separator and the reactor tank and contains an open/close automatic valve (outside the reactor) just before all the pipes are connected to a header.

This header collects the anaerobic effluent recycle flow from each three phase separator and discharges it to the conditioning tank. This can be further explained with the following example:
Design raw wastewater flow 100 m3/h.
Actual wastewater flow 60 m3/h
Feed flow to the reactor 150 m3/h, so 50 m3/h anaerobic effluent recycle under design conditions
Effective three phase separator surface 15 m2.
The reactor has 3 three phase separators of equal lengths.

In the prior art situation, the effective surface load on the three phase separator, both for the design and actual situation, is 150/15=10 m$^3$/m$^2$·hour. According to the preferred embodiment of the invention, with the improved recycle location, the effective surface load on the three phase separator is $100/15=6.67$ m$^3$/m$^2$·hour under design conditions and only $60/15=4$ m$^3$/m$^2$·hour under actual operating conditions.

According to a preferred embodiment, the open/close valves in the recycle line have for example the following sequence:

At any time 2 valves are closed and 1 is open.

Every 5 minutes there is a change over: One of the closed valves opens and at the same time the valve which is open closes.

So at any moment the full recycle flow is taken from one of the 3 three phase separators at 50 m$^3$/h under design conditions and maximum 150 m3/h in case there is no raw wastewater feed flow.

The result of these fluctuating flows over time is:

(More) equal recirculation from each three phase separator and over the lengths of each three phase separator.

Automatic cleaning of the three phase separator, with less risk for blockage.

Moreover, the combination of extra settling surface and the new means for anaerobic effluent recycle results into a more effective extraction of the settled solids at the bottom of three phase separator. This also reduces the risk of blockage.

In case a separator or part thereof is specifically dedicated for recycle water, it is possible to have different kind of internals than in the separators for the effluent, or to use no internals at all.

The means of anaerobic effluent extraction gives also the possibility for in-process cleaning of the three phase separator(s) and its internals by introduction of a back flow of water or (bio) gas recycles through the same extraction pipe and holes or slots.

This is of special importance when a reactor is operated under biogas pressure (completely closed) as under such conditions it will be very inconvenient to open a reactor for inspection or cleaning purposes.

The three phase separator(s) according the present invention will make use of multiple (2 to 10) biogas separation baffles plates similar as they are used in the Biothane UASB and Biobed three phase separators. The settled solids from the three phase separator will positively be returned to the reactor as a result of a by gravity difference induced circulation flow (mammouth stream).

A further important preferred feature related to this innovative anaerobic sludge bed process and reactor according to the invention is related to the improvement of the mixing and distribution of the to be treated wastewater with (all of) the available biomass.

Typically the influent distribution system will be executed with 1 nozzle per 1 up to 4 m$^2$ reactor surface and having an even number of nozzles equally distributed over the reactor surface, using strings with several nozzles at one string.

The special feature of this embodiment of the invention is that the reactor will be executed with several of these influent distributions over its height.

Not only will this give a better distribution and mixing of the reactor feed flow with the available biomass, it will also, very effectively, break stagnant sludge layers to prevent building up of biogas in gas pockets which may result in irregular and undesired biogas production flows from the reactor.

Preferably a reactor will have at least 1, preferably 2 to 5 independent operating influent distribution systems. These systems will be located at different planes over the height of the reactor. In general the first system is located near the bottom of the reactor. The other influent distribution systems will be located above the first one at locations between 15 and 55% of the height of the reactor.

In a typical configuration one system is located at the bottom of the reactor and further one at respectively 2, 4 and 6 m from the bottom.

The influent distribution system can be executed as a modulating min/max flow system with preferably horizontal outflow for better mixing and breaking-up of the sludge bed (to prevent biogas entrapment). Typically 0-40% of the flow is directed to one half of the nozzles and as a result 100-60% to the other half. The preferred change over from min to max is every 1 to 5 minutes.

In a set-up using two influent distribution systems typically 20 to 80% of the flow is directed to the bottom influent distribution system and as a result 80 to 20% of the flow to the influent distribution system at higher elevation.

In case more than two influent distribution systems are used, the distribution of the influent over the systems is 20-80% to the bottom influent distribution system and the rest, so 80-20% is distributed equally over the rest of the influent distribution systems at higher elevations.

This embodiment is further explained in the following example:

Design raw wastewater flow 100 m$^3$/h.

Actual wastewater flow 60 m$^3$/h

Feed flow to the reactor 150 m$^3$/h, so 50 m$^3$/h anaerobic effluent recycle under design conditions Reactor 600 m$^3$, 15 m high so 40 m$^2$ reactor surface The reactor has 3 influent distribution systems over its height, one near the bottom, one at 2 m and one at 4 m height Each influent distribution system is equipped with 4 strings and 10 nozzles in total.

½ of the reactor feed flow (so 75 m$^3$/h) is directed to the bottom influent distribution system and ¼ (so 37.5 m$^3$/h) is directed to the influent distribution system at respectively 2 and 4 m.

Each Influent distribution system is operated with a min/max flow distribution of 30%/70% as explained above.

The various aspects of the invention are now elucidated on the basis of the attached figures, wherein FIG. 1 gives the general process arrangement consisting of a reactor and a conditioning tank, FIG. 2a a side view of a three phase separator, FIG. 2b a top view of the separator, FIG. 2c another top view of the separator, FIG. 3 an upflow reactor with multi level influent distributions systems, FIGS. 4a and 4b two embodiments of direct recycle pipes, FIG. 5 a top view of an upflow reactor with multiple three phase separators, and FIG. 6 a recycle from the top of the reactor using a gas deflecting plate.

Figure 1:
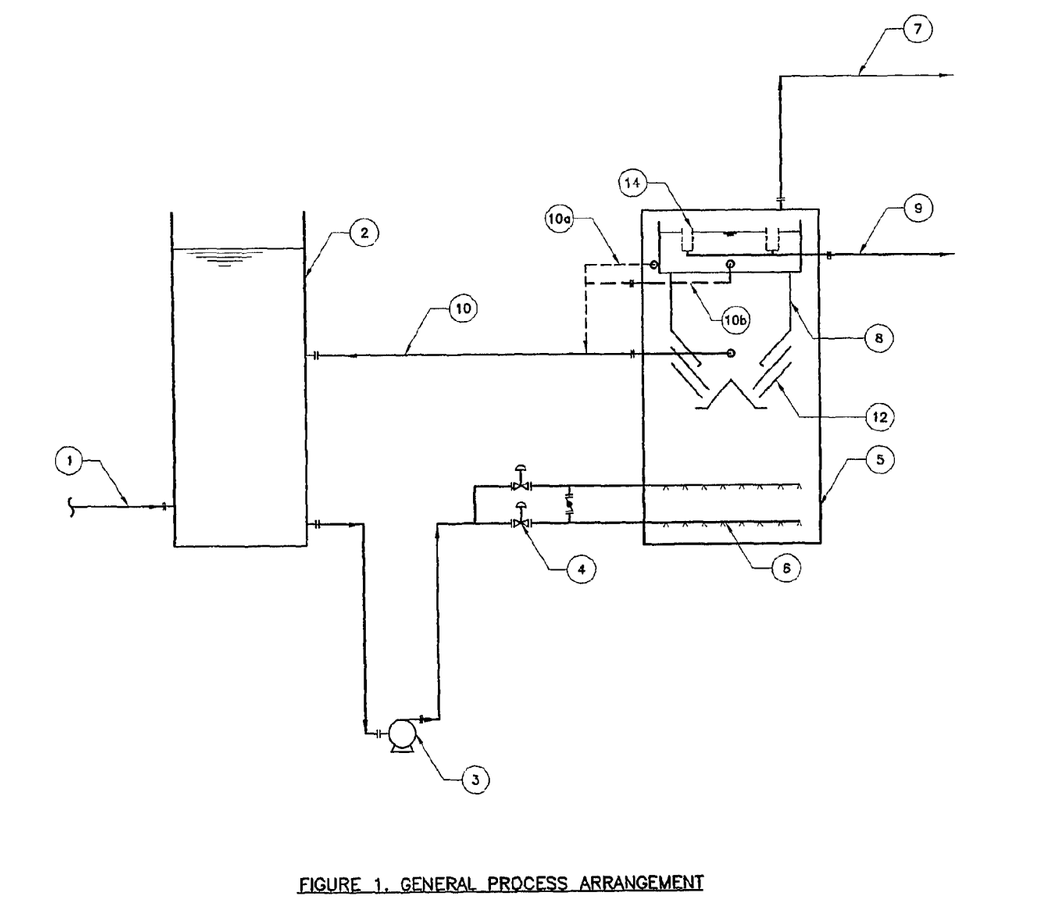

In FIG. 1, raw waste water 1 is fed to conditioning tank 2, where it is combined with recycle water 10 (gravity flow from the upflow reactor 5). In the conditioning tank 2 the water is conditioned (temperature, pH, nutrients addition) by means not shown. Reactor feed pump 3 pumps the conditioned water via valves 4 to the influent distribution systems 6 near the bottom of reactor 5.

The waste water rises in the reactor, wherein a sludge bed is present consisting of mainly granular sludge. Due to the anaerobic breakdown of the contaminants in the waste water biogas is formed and a mixture of solid, liquid and gas develops. The mixture enters the three phase separator 8, where the gas is removed via the tilted baffles 12. The solids in the mixture settle through the separator and are returned to the reactor. Cleaned effluent is withdrawn through 9. The gas produced is removed through line 7. Recycle is withdrawn (by gravity) through line 10. In the alternative the recycle (all by gravity) can be withdrawn form location 10a (outside the three phase separator) or 10b (from part of the three phase separator).

Figure 2A:
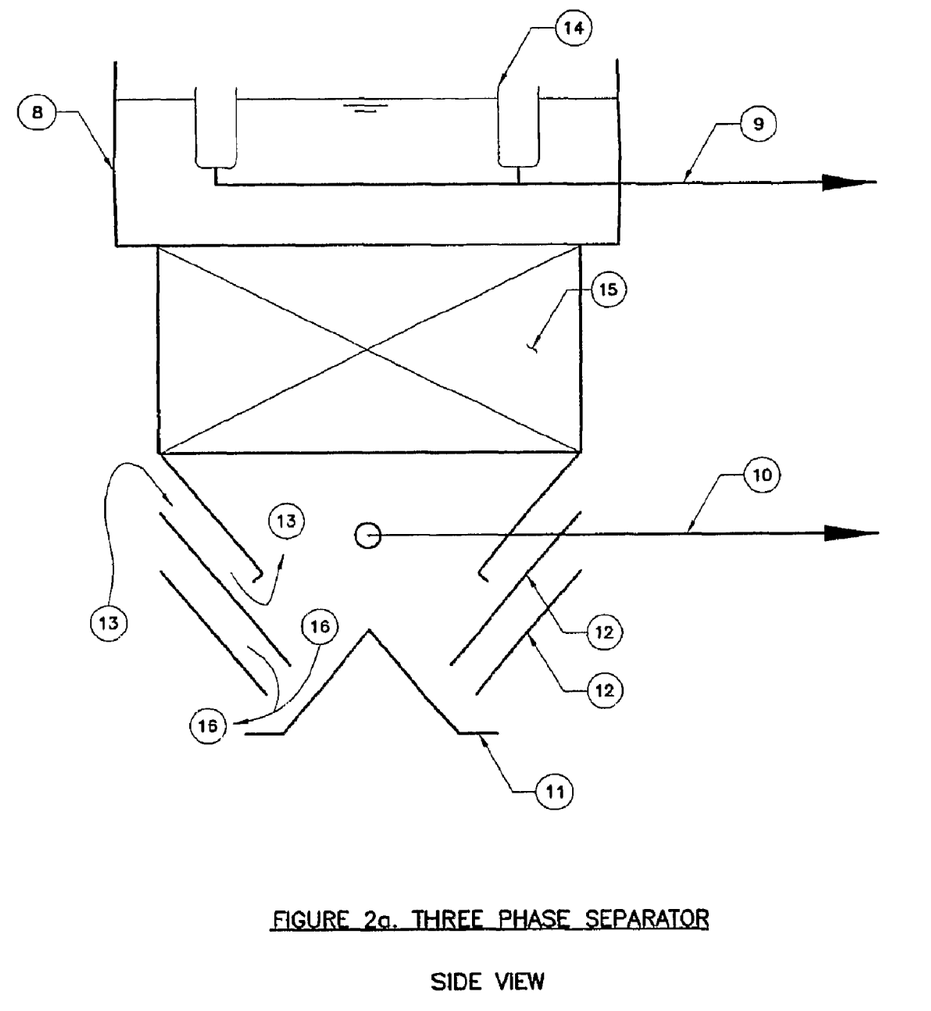

FIG. 2a gives a detailed view of three-phase separator 8, wherein 13 denotes the water flow inlet. This water further contains gas and solids and flows between the multiple biogas separation baffle plates 12. Due to the turbulent, downward flow of the mixture attached gas is separated from the solids. Part of the mixture flows down through the section between the bottom of the baffle plates and the lower gas gap 11 and part flows upward into internal section 15 of the separator 8. Internal section 15 is preferably provided with internals such as tilted tubes or titled plates to improve the liquid-solid separation. The solids settle in downward direction and flow down back into the reactor through section 16. Liquid flows upward out of the internal section 15 and via overflow launders 14 effluent is removed through line 9. The recycle can be withdrawn from the bottom part of the three phase separator 8 and next via pipe 10 gravity flow to the conditioning tank.

Figure 2B:
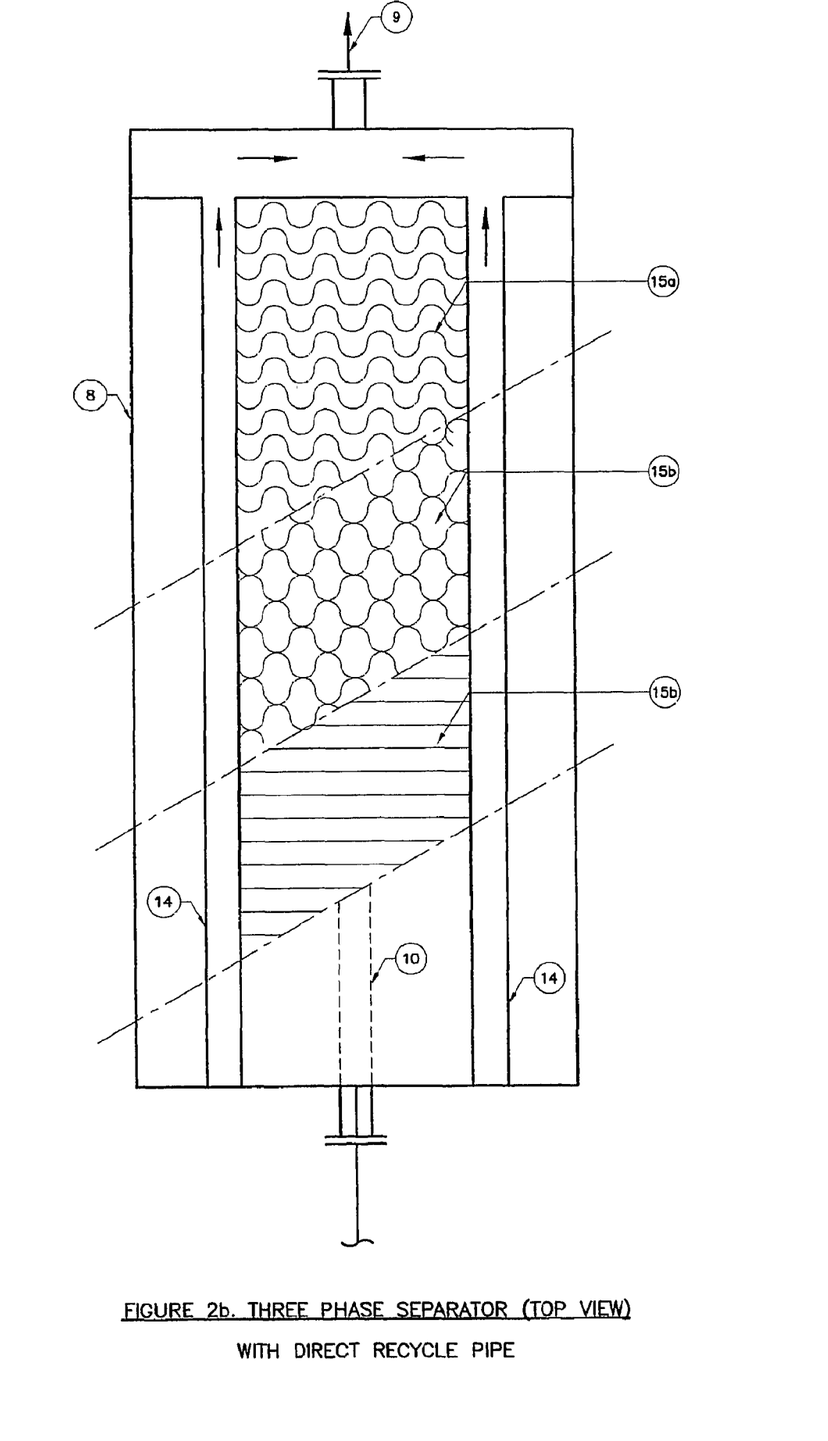

In FIG. 2b a top view of the three phase separator 8 has been given, wherein the numeric indications correspond to the numeric indications in the description of FIGS. 1 and 2a. In this figure various possibilities for tilted plates have been given. 15a denote corrugated tilted plates, 15b denote tilted tubes and 15c denote tilted flat plates.

Figure 2C:
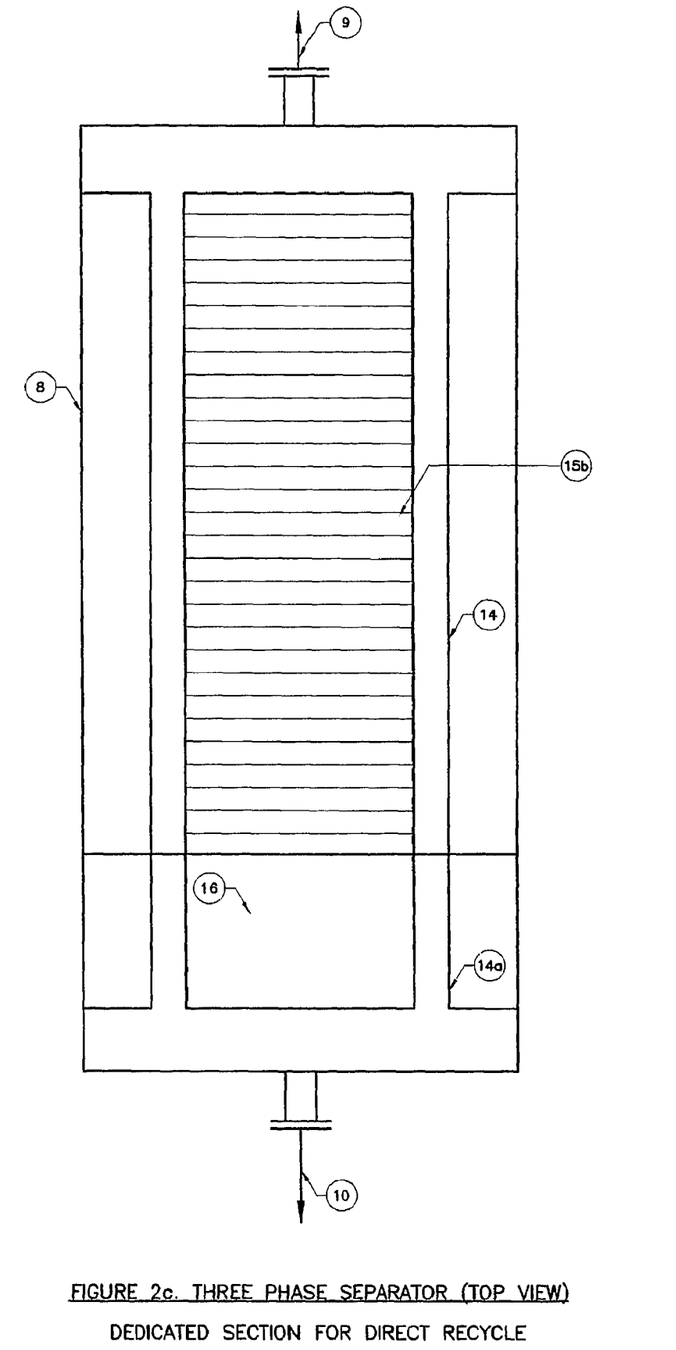

In FIG. 2c a top view of a three phase separator has been given, which has a specific dedicated section for collecting recycle. This section has been denoted as 16. This section can be with or without internals. The water from section 16 flows through overflow launders 14a to recycle pipe 10. The effluent flows via the launders 14 to effluent discharge pipe 9.

Figure 3:
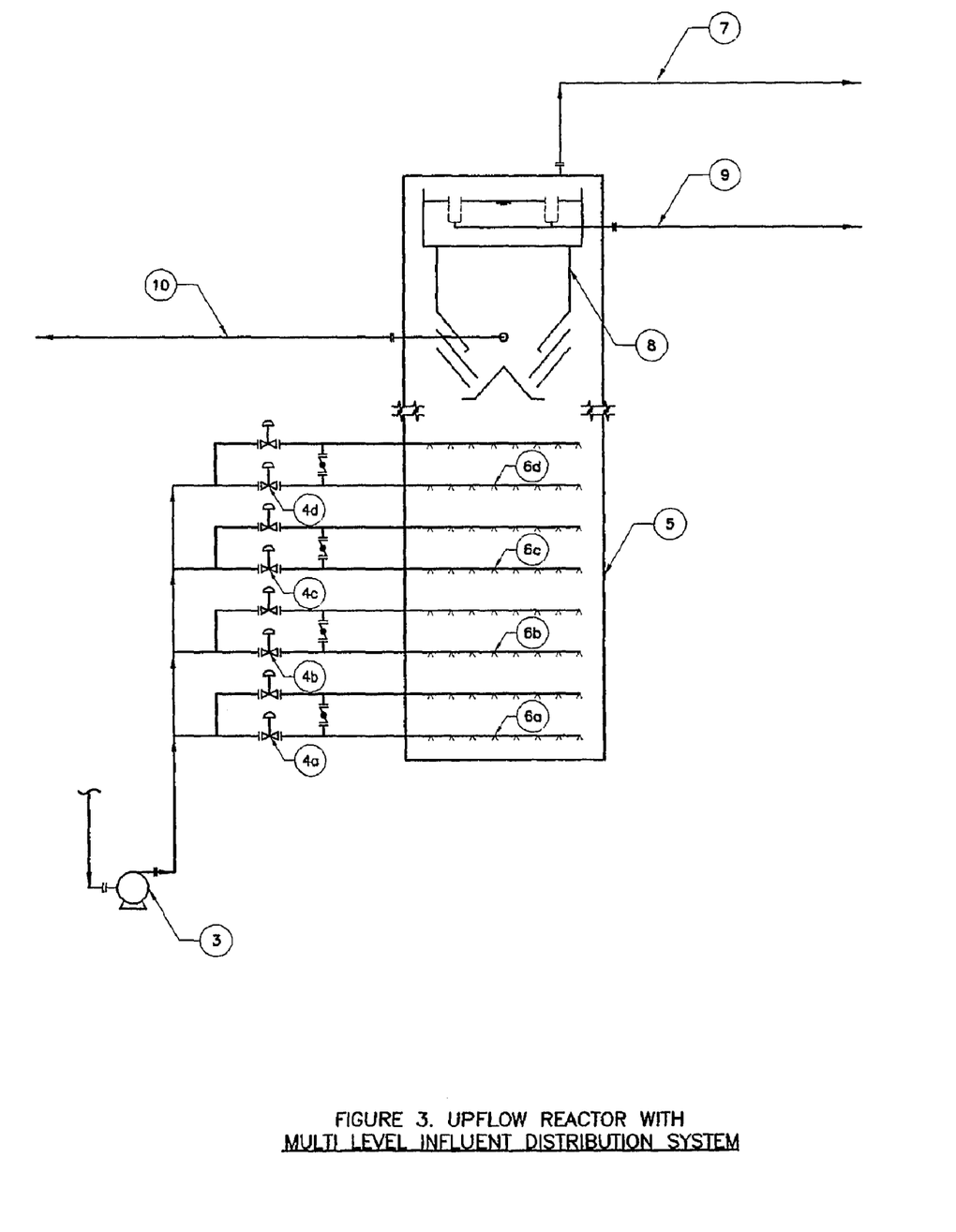

In FIG. 3 a multiple influent distribution system has been described, having four distribution systems 6a, 6b, 6c en 6d. The amount of water to the various discharge pipes is regulated via valves 4a, 4b, 4c and 4d.

Figure 4A:
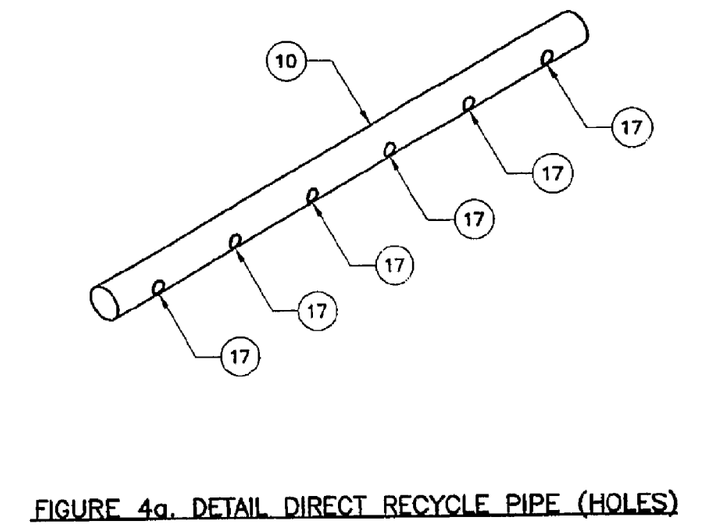
Figure 4B:
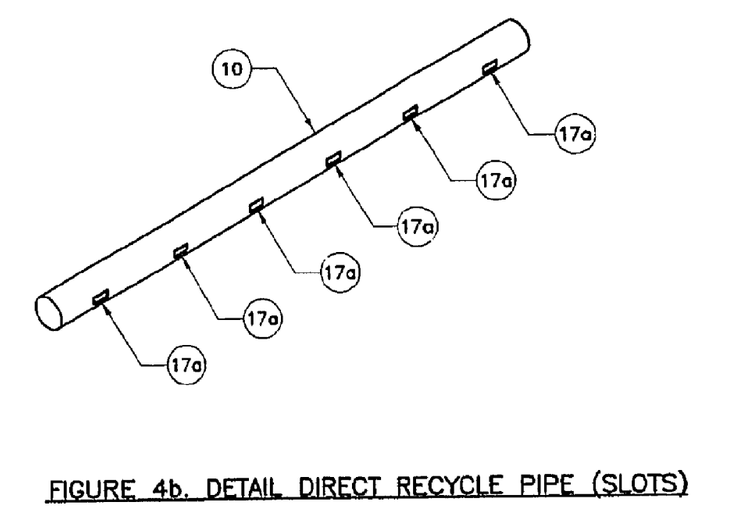

FIGS. 4a and 4b show details of direct recycle pipes, which are located preferably in the bottom of the three phase separator 10. FIG. 4a shows the pipe having orifices 17. FIG. 4b shows slots 17a.

Figure 5:
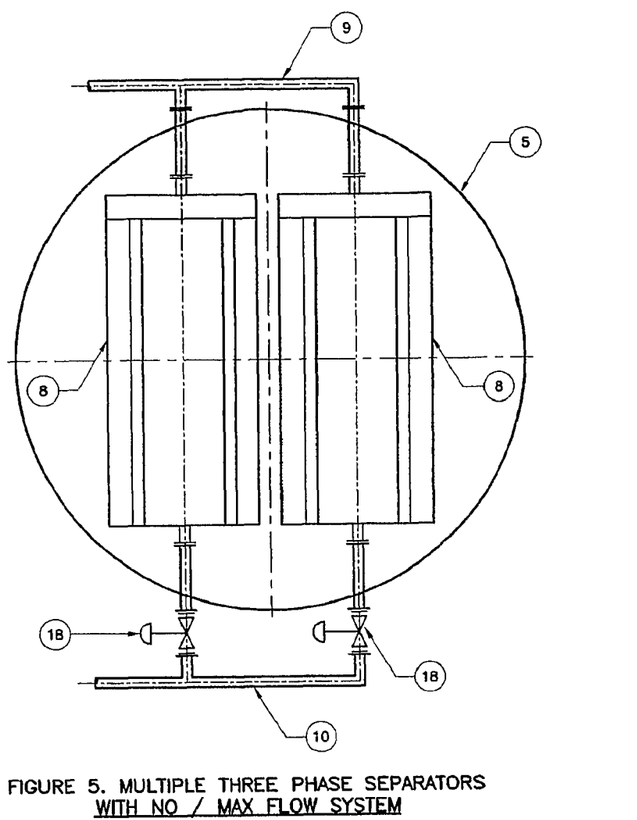

In FIG. 5 a top view of multiple three phase separators in an upflow reactor are shown. In this embodiment two separators have been shown, but it is also possible to include more separators. Each of the separators is connected through direct recycle pipes with the recycle line 10. The recycle pipes have been provided with valves, which can either have an open-close position or can be used to regulate the flow from 0 to 100%, either gradually or stepwise.

Figure 6:
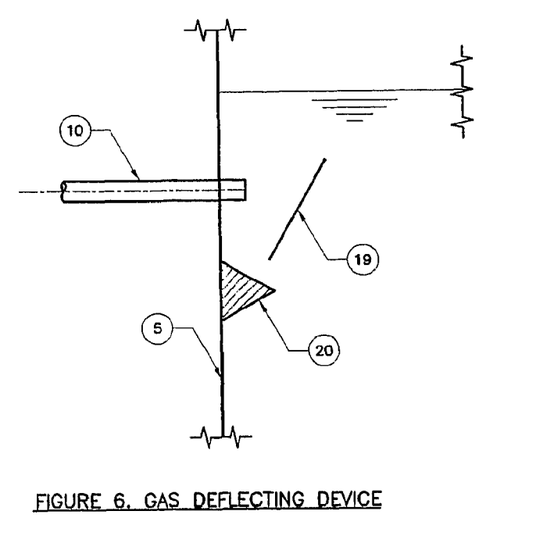

In FIG. 6 a possible embodiment of a gas deflecting outside the three phase separator has been shown. This device consists of gas deflection means 19 and 20, which are located before the withdrawal means 10.

The invention claimed is:

1. A process for the anaerobic purification of waste water using a sludge bed system, which process comprises
   feeding waste water and optionally recycle water to the lower part of an upflow reactor comprising a three phase separator, said reactor containing mainly granular biomass thus producing biogas in the treatment;
   passing the resulting gas/liquid/solid mixture upward through the separator;
   separating the gas and solid from the liquid in said separator and thereby generating an effluent;
   withdrawing the effluent from the top of the separator,
   separating the solids from the liquid in a portion of the separator above the separation of the gas from the liquid phase,
   wherein tilted plates, tubes or other tilted internals are installed in said portion to increase the effective settling surface.

2. The process according to claim 1, wherein the internals are positioned in an angle of 50 to 70°.

3. The process according to claim 1, wherein recycle water is withdrawn separately from the effluent, either from the three phase separator or from the top of the reactor outside the three phase separator.

4. The process according to claim 1, wherein the recycle water is introduced, into a conditioning tank into which also the (raw) waste water is introduced, and from which the combined flow of waste water and recycle is introduced into the reactor.

5. The process according to claim 1, wherein the tilted plates, tubes or other tilted internals in the three phase separator body increase the effective settling surface with a factor 2 to 10.

6. The process according to claim 1, wherein multiple-biogas separation baffle plates are present at the inlet of the three phase separator to prevent that biogas enters the actual settling portion of the three phase separator and provides effective separation of the biogas (bubbles) attached to the solid particles.

7. The process according to claim 6, wherein 2 to 10 biogas separation baffles plates are present.

8. The process according to claim 1, wherein the feed to the reactor is introduced therein through a multi level influent distribution system.

9. The process according to claim 8, wherein 2 to 5 levels of the influent distribution system are present.

10. The process according to claim 8, wherein a first influent distribution system is located near the bottom of the reactor and other influent distribution system or influent distribution systems are located above the first one at locations between 15 and 55% of the height of the reactor.

11. An upflow reactor suitable for the process of claim 1, which reactor comprises a reactor tank having incorporated therein a three phase separator for separating gas, solid and liquid, which three phase separator is present in the upper part of the said reactor,
   at least one influent distribution entry for introducing a flow of waste water into the reactor, in the lower part of the reactor,
   at least one effluent withdrawal exit at the top of said separator for withdrawing anaerobic effluent from the separator, wherein the portion of the three phase separator, above the separation of the gas from the liquid phase, has tilted plates, pipes or other tilted internals installed.

12. The reactor according to claim 11, wherein the internals are positioned in an angle of 50 to 70°.

13. The reactor according to claim 11, wherein a conditioning tank is present, provided with waste water feed means, recycle feed means, connected with the recycle withdrawal means of the reactor, and feed means to feed the recycle and waste water flow to the reactor.

14. The reactor according to claim 11, which further includes at least one recycle withdrawal exit for withdrawing recycle water, which exit is separate from the effluent withdrawal exit and which recycle withdrawal exit is designed to withdraw water from the three phase separator or from the top of the reactor outside the three phase separator.

15. The reactor according to claim 11, wherein multiple-biogas separation baffle plates are present at the entrance of the three phase separator.

16. The reactor according to claim 15, wherein 2 to 10 biogas separation baffle plates are present.

17. The reactor according to claim 11, wherein the feed to the reactor is a multiple level influent distribution system.

18. The reactor according to claim 17, wherein 2 to 5 influent distribution systems are present at different levels in the reactor.

19. A three phase separator, suitable for use in the process of claim 1, which separator comprises a main separator body, at least one entry for a gas-liquid-solid mixture,
- single or multiple-biogas separation baffle plates for separating gas from the mixture,
- tilted plates, pipes or other tilted internals installed in the three phase separator body above the separation of the gas from the liquid phase, and
- exit for withdrawing effluent water from the top of the three phase separator.

20. The separator of claim 19 which further includes at least one recycle water exit.

21. A three phase separator, suitable for use in the reactor of claim 11, which separator comprises a main separator body, at least one entry for a gas-liquid-solid mixture,
- single or multiple-biogas separation baffle plates for separating gas from the mixture,
- tilted plates, pipes or other tilted internals installed in the three phase separator body, above the separation of the gas from the liquid phase, and
- exit for withdrawing effluent and from the top of the three phase separator.

22. The separator of claim 20 which further includes at least one recycle water exit.

* * * * *

UNITED STATES PATENT AND TRADEMARK OFFICE
CERTIFICATE OF CORRECTION

| | |
|---|---|
| PATENT NO. | : 8,043,506 B2 |
| APPLICATION NO. | : 12/159986 |
| DATED | : October 25, 2011 |
| INVENTOR(S) | : Robertus Johannes Frankin et al. |

It is certified that error appears in the above-identified patent and that said Letters Patent is hereby corrected as shown below:

On the title page, Item (73) the following Assignee information should be deleted:

"(73) Assignee: BIOTHANE SYSTEMS INTERNATIONAL B.V.,
            Delft (NL)"

On the title page, Item (73) the following Assignee information should be inserted:

-- (73) Assignee: VEOLIA WATER SOLUTIONS & TECHNOLOGIES SUPPORT,
            Saint Maurice (FR) --

Signed and Sealed this
Twenty-fourth Day of April, 2012

David J. Kappos
*Director of the United States Patent and Trademark Office*